(12) United States Patent
Harris et al.

(10) Patent No.: US 12,678,521 B2
(45) Date of Patent: Jul. 14, 2026

(54) APPARATUS FOR IRRADIATION

(71) Applicant: AquiSense Inc., Erlanger, KY (US)

(72) Inventors: Theodore Robert Harris, Charlotte, NC (US); Jennifer Godwin Pagan, Charlotte, NC (US); Paolo Batoni, Charlotte, NC (US); John Robert Krause, Charlotte, NC (US)

(73) Assignee: AquiSense Inc., Erlanger, KY (US)

( * ) Notice: Subject to any disclaimer, the term of this patent is extended or adjusted under 35 U.S.C. 154(b) by 736 days.

(21) Appl. No.: 17/750,791

(22) Filed: May 23, 2022

(65) Prior Publication Data

US 2022/0395592 A1 Dec. 15, 2022

Related U.S. Application Data

(63) Continuation of application No. 14/102,969, filed on Dec. 11, 2013, now Pat. No. 11,338,048.

(Continued)

(51) Int. Cl.
| | |
|---|---|
| *A61L 2/10* | (2026.01) |
| *A61L 2/084* | (2026.01) |

(Continued)

(52) U.S. Cl.
CPC ................. *A61L 2/084* (2013.01); *A61L 2/10* (2013.01); *A61L 2/16* (2013.01); *A61L 9/20* (2013.01); *C02F 1/325* (2013.01); *C02F 2305/10* (2013.01)

(58) Field of Classification Search
None
See application file for complete search history.

(56) References Cited

U.S. PATENT DOCUMENTS

2005/0152146 A1* 7/2005 Owen .................. G03F 7/7005
362/241
2008/0297027 A1* 12/2008 Miller ................... H05B 45/20
313/498

(Continued)

FOREIGN PATENT DOCUMENTS

JP 2008522356 A * 6/2008
WO WO-2012123412 A1 * 9/2012 .............. A61L 2/10

OTHER PUBLICATIONS

English machine translation of JP 2008522356 A provided by Clarivate, original document published 2008 (Year: 2008).*

(Continued)

*Primary Examiner* — Holly Kipouros
(74) *Attorney, Agent, or Firm* — Knobbe, Martens, Olson & Bear, LLP

(57) ABSTRACT

An irradiation apparatus configured to be coupled to an irradiation chamber containing a material to be irradiated, comprising: a support structure; one or more radiation sources coupled to the support structure; and a heat exchange mechanism thermally coupled to the one or more radiation sources. The heat exchange mechanism comprises one or more of a thermoelectric cooling device, a vapor chamber, a heatsink, a heat dissipation structure, a fan, and a cooling coating. The one or more radiation sources comprise one or more UV radiation sources, one or more UV-C radiation sources, one or more visible radiation sources, or a combination thereof. Optionally, the one or more radiation sources comprise a plurality of radiation sources arranged in an array. Optionally, the one or more radiation sources deliver a combination of wavelengths to the material to be irradiated.

19 Claims, 10 Drawing Sheets

Related U.S. Application Data

(60) Provisional application No. 61/735,734, filed on Dec. 11, 2012.

(51) Int. Cl.
| | |
|---|---|
| *A61L 2/16* | (2006.01) |
| *A61L 9/20* | (2006.01) |
| *C02F 1/32* | (2023.01) |

(56) References Cited

U.S. PATENT DOCUMENTS

| | | | | |
|---|---|---|---|---|
| 2010/0296971 A1 * | 11/2010 | Gaska | .................... | C02F 1/325 |
| | | | | 422/62 |
| 2014/0050612 A1 * | 2/2014 | Kneissl | .................... | A61L 2/10 |
| | | | | 250/435 |

OTHER PUBLICATIONS

Rodriguez et al. (Design of a UV—A LED Photocatalytic Oxidation Reactor for Testing Spacecraft Potable Water Disinfection Technologies), SAE technical paper 09ICES-0040, 2009 (Year: 2009).*
Wegelin et al. (Solar water disinfection: scope of the process and analysis of radiation experiments), J Water SRT-Aqua, vol. 43 No. 3, pp. 154-169, 1994 (Year: 1994).*

* cited by examiner

APPARATUS FOR IRRADIATION

CROSS-REFERENCE TO RELATED APPLICATION

The present patent application/patent claims the benefit of priority of U.S. Provisional Patent Application No. 61/735, 734, filed on Dec. 11, 2012, and entitled "APPARATUS FOR IRRADIATION," the contents of which are incorporated in full by reference herein.

STATEMENT OF GOVERNMENT SUPPORT

The present invention was made with U.S. Government support pursuant to Award No. IIP-1059286 by the National Science Foundation (American Society for Engineering Education). Accordingly, the U.S. Government has certain rights in the present invention.

FIELD OF THE INVENTION

The present invention relates generally to systems and methods for disinfection by irradiation. More specifically, the present invention relates to an apparatus for irradiation.

BACKGROUND OF THE INVENTION

It is well known to those of ordinary skill in the art that fluids, including liquids and gases, as well as solids, may be disinfected using radiation, such as ultraviolet (UV) radiation. In the past, this radiation was provided by mercury (Hg) discharge-based point sources or the like. More recently, light emitting diodes (LEDs), which emit radiation when a current is applied to them, have been used to provide uniform irradiation in specially designed chambers or flow cells. Of key commercial interest is the disinfection of water and air using radiation.

UV LEDs emit UV radiation that interacts with biological structures, making them suitable for germicidal applications. Advantageously, UV LEDs have very short warm-up times and have no zero-flow limitations. They can also be selected and adjusted in terms of peak emission wavelength and wavelength combinations to deliver an optimized radiation dose to a given microorganism.

The use of UV LEDs in the fluid treatment market is poised for explosive growth, as water supplies continue to be tapped by growing populations and the pathogen contamination of such water supplies becomes a growing industry and consumer concern. Approximately 1.8 million deaths worldwide are directly related to waterborne diseases, and 88% of those infections are due to unsafe water supplies, sanitation, and hygiene. Chemical and drug resistance of pathogenic microorganisms that cause hospital acquired infections is also a growing problem. For example, MRSA is emerging worldwide as a community acquired infection. It is often not possible to add chlorine and other disinfecting chemicals in high purity applications to defeat such pathogenic organisms, therefore innovative engineered UV disinfection systems may be one of the few remaining means to resolve this problem. In addition, the increased use of mercury free UV technologies would result in reduced hazardous environmental risks, and reduced costs associated with hazardous material disposal.

Thus, UV LEDs can be used to perform the same functions as Hg-based UV lamps and the like; however, they are an environmentally friendly alternative because they do not contain heavy metals, and they do not require special handling or disposal. Moreover, their pseudo-instantaneous on-off operation (as low as about 9 ns with gigahertz back-end electronics) and their reduced footprint (typically about 0.3 mm2 to about 0.5 mm2) enable greater design freedom for applications with size, voltage, architecture, and rapid on-off operation constraints. In other words, UV LEDs enable a paradigm shift in the collective technological conscience as to the design of UV water and air disinfection systems.

What is still needed in the art, however, is an improved apparatus for irradiation that can utilize tailored peak emission wavelengths and combinations of wavelengths, that incorporates an adequate thermal management system, that allows for the recuperation of thermal emissions, and that may be used with a variety of housings or flow cells, all while maintaining a compact footprint, among other things.

BRIEF SUMMARY OF THE INVENTION

In various exemplary embodiments, the present invention provides such an improved apparatus for irradiation that utilizes tailored peak emission wavelengths and combinations of wavelengths, that incorporates an adequate thermal management system, that allows for the recuperation of thermal emissions, and that may be used with a variety of housings or flow cells, all while maintaining a compact footprint, among other things. Optionally, the apparatus may be combined with a detector mechanism and other electronics and is dynamically reconfigurable.

In one exemplary embodiment, the present invention provides an irradiation apparatus configured to be coupled to an irradiation chamber containing a material to be irradiated, comprising: a support structure; one or more radiation sources coupled to the support structure; and a cooling mechanism thermally coupled to the one or more radiation sources. The cooling mechanism (i.e. heat exchanger) comprises one or more of a thermoelectric cooling device, a vapor chamber, a heatsink, a heat dissipation structure, a fan, and a cooling coating. Optionally, the cooling mechanism further comprises a thermoelectric heat recovery mechanism. The irradiation apparatus also comprises a moisture seal and desiccant disposed adjacent to the one or more radiation sources. The one or more radiation sources comprise one or more UV radiation sources, one or more UV-C radiation sources, one or more visible radiation sources, or a combination thereof. Optionally, the one or more radiation sources comprise a plurality of radiation sources arranged in an array. Preferably, one or more wavelengths of the one or more radiation sources are dynamically adjustable. Optionally, one or more wavelengths of the one or more radiation sources are selected based on an identification of a contaminant in the material to be irradiated. Optionally, the one or more radiation sources deliver one or more wavelengths to the material to be irradiated that induce fluorescence in the material to be irradiated thereby allowing for the identification of the contaminant in the material to be irradiated. Optionally, the one or more radiation sources deliver a combination of wavelengths to the material to be irradiated. Optionally, one or more wavelengths of the one or more radiation sources are selected to both saturate an absorption mechanism of nucleocapsids in the material to be irradiated and target a peak absorption of nucleic acid in the material to be irradiated. Optionally, the one or more radiation sources deliver one or more wavelengths to a semiconductor material disposed substantially adjacent to the material to be irradiated thereby causing a disinfection agent to be generated in proximity of the material to be irradiated. The irradiation apparatus may still further comprises a radiation intensity feedback mechanism, such as a photodiode, CCD, etc.

In another exemplary embodiment, the present invention provides an irradiation method for irradiating a material to be irradiated disposed in an irradiation chamber, comprising: providing a support structure coupled to the irradiation chamber; providing one or more radiation sources coupled to the support structure; and providing a cooling mechanism thermally coupled to the one or more radiation sources. The cooling mechanism (i.e. heat exchanger) comprises one or more of a thermoelectric cooling device, a vapor chamber, a heatsink, a heat dissipation structure, a fan, and a cooling coating. Optionally, the cooling mechanism further comprises a thermoelectric heat recovery mechanism. The irradiation method also comprises providing a moisture seal and desiccant disposed adjacent to the one or more radiation sources. The one or more radiation sources comprise one or more UV radiation sources, one or more UV-C radiation sources, one or more visible radiation sources, or a combination thereof. Optionally, the one or more radiation sources comprise a plurality of radiation sources arranged in an array. Preferably, one or more wavelengths of the one or more radiation sources are dynamically adjustable. Optionally, one or more wavelengths of the one or more radiation sources are selected based on an identification of a contaminant in the material to be irradiated. Optionally, the one or more radiation sources deliver one or more wavelengths to the material to be irradiated that induce fluorescence in the material to be irradiated thereby allowing for the identification of the contaminant in the material to be irradiated. Optionally, the one or more radiation sources deliver a combination of wavelengths to the material to be irradiated. Optionally, one or more wavelengths of the one or more radiation sources are selected to both saturate an absorption mechanism of nucleocapsids in the material to be irradiated and target a peak absorption of nucleic acid in the material to be irradiated. Optionally, the one or more radiation sources deliver one or more wavelengths to a semiconductor material disposed substantially adjacent to the material to be irradiated thereby causing a disinfection agent to be generated in proximity of the material to be irradiated.

BRIEF DESCRIPTION OF THE DRAWINGS

The present invention is illustrated and described herein with reference to the various drawings, in which like reference numbers are used to denote like apparatus components, as appropriate, and in which.

DETAILED DESCRIPTION OF THE INVENTION

Figure 1:
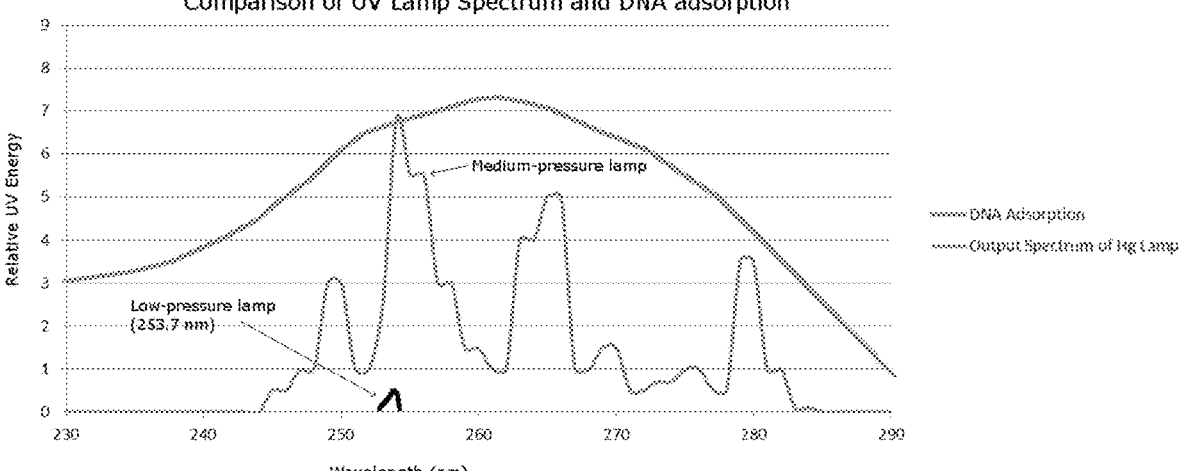
FIG. 1 is a plot illustrating the UV absorption curve of deoxyribonucleic acid (DNA)

Referring now specifically to FIG. 1, by way of enabling background, DNA has a peak absorption at about 260 nm, but the absorption curve is broad, with the majority of UV absorption occurring between about 240 nm and about 280 nm. Low and medium pressure Hg lamps have emission peaks at about 253.7 nm, with medium pressure Hg lamps having emission peaks that are narrow and sporadic across the peak microbicidal region of DNA. By comparison, UV LEDs have broadband deep UV emission that can be tailored for peak emission at about 260 nm to provide the maximum dose more effectively than Hg lamps.

Experimentally determined UV rate constants reported in the literature indicate that some microorganisms are more resistant to UV irradiation than other microorganisms. Several factors affect a microorganism's resistance to UV, including double stranded vs. single stranded DNA, length of DNA, high cytosine and guanine (CG) content of DNA, microorganism size, and shielding effects by capsid proteins, lipids, or other packaged viral proteins. The commonly accepted strategy to achieve disinfection by means of UV irradiation is the "brute force" approach, in other words, the use of Hg UV lamps having a similar, if not identical, fixed, non-variable optical output spectrum for any possible microorganism, while adjusting the dose in mJ per unit area that is experimentally known to be required for inactivating the same microorganism. This strategy has evolved into a scenario where only a limited variety of UV sources are available. However, UV LEDs and the like are progressively changing this because they can provide tailored UV wavelengths.

Figure 2:
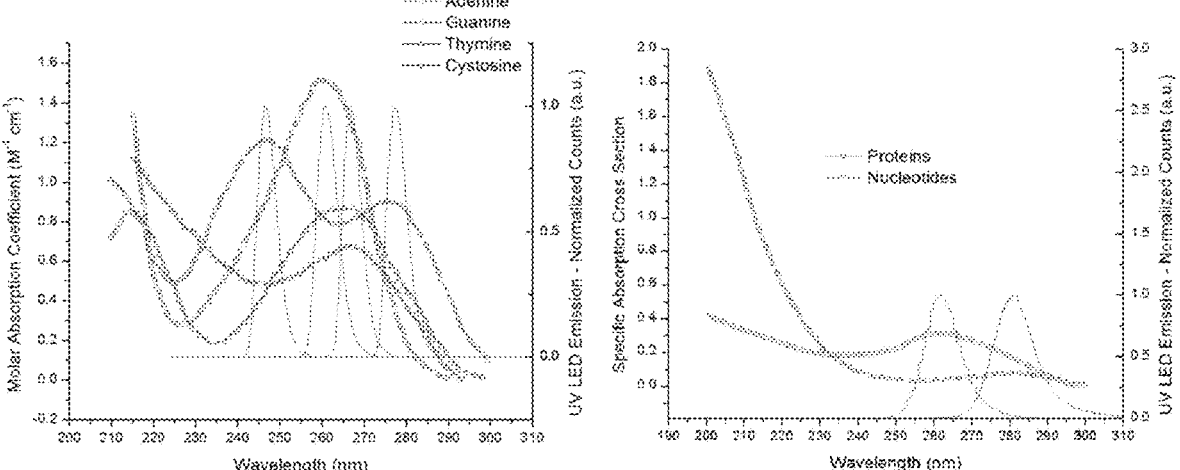
FIG. 2 is a series of plots illustrating the simultaneous use of UV wavelengths to saturate the absorption of UV photons by the proteins of nucleocapsids and allow UV photons to be delivered to DNA and the simultaneous use of UV wavelengths to target nucleotide pairs.

Different wavelengths can be used to saturate the absorption mechanism of nucleocapsids, which exhibit a peak absorption centered at around 280 nm, while also targeting the peak absorption of nucleic acid at around 265 nm, as illustrated in FIG. 2. The spectral absorption cross-section of proteins and nucleotides is comparable at about 280 nm, and a system that solely provides 280-nm photons would not be effective in impacting the nucleic acid. Thus, the present invention uses simultaneous wavelengths to target nucleotide pairs and exploit the lesser stable adenine-thymine pairs, or more stable cytosine-thymine pairs. For instance, wavelengths ranging from about 240-275 nm, or about 275-290 nm, can be simultaneously used with wavelengths ranging from about 255 nm-290 nm, and about 290 nm-320 nm, to saturate the absorption mechanism of nucleocapsids, while allowing about 240 nm-290-nm photons to be delivered to guanine and thymine without being sequestered by the nucleocapsids. Similarly, wavelengths ranging from about 250-275 nm can be simultaneously used with wavelengths ranging from about 255 nm-290 nm, and about 290 nm-320 nm to saturate the absorption mechanism of the nucleocapsids, and allow about 250 nm-275-nm photons to be delivered to adenine and thymine without being sequestered by the nucleocapsids.

Figure 3:
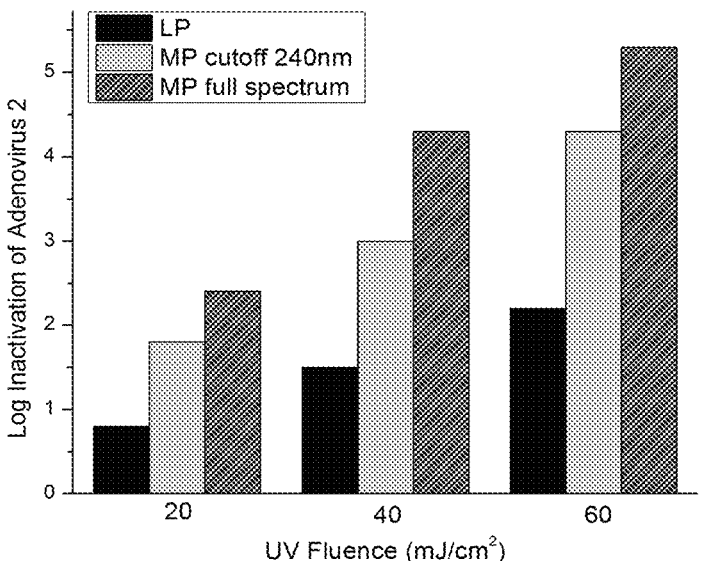
FIG. 3 is a plot illustrating the inactivation of adenoviruses with polychromatic UV radiation versus monochromatic UV radiation.

Investigations of the enhanced UV inactivation of adenoviruses under polychromatic medium pressure Hg lamps have indicated that the UV flux required to achieve 4-log inactivation of adenovirus type 40 is reduced by approximately 70% when compared to the required flux using monochromatic UV 253.7 nm irradiation from conventional low pressure Hg lamps. The implications are that the simultaneous irradiation with wavelengths emitted by the polychromatic UV lamps are significantly more effective, as illustrated in FIG. 3.

Figure 4:
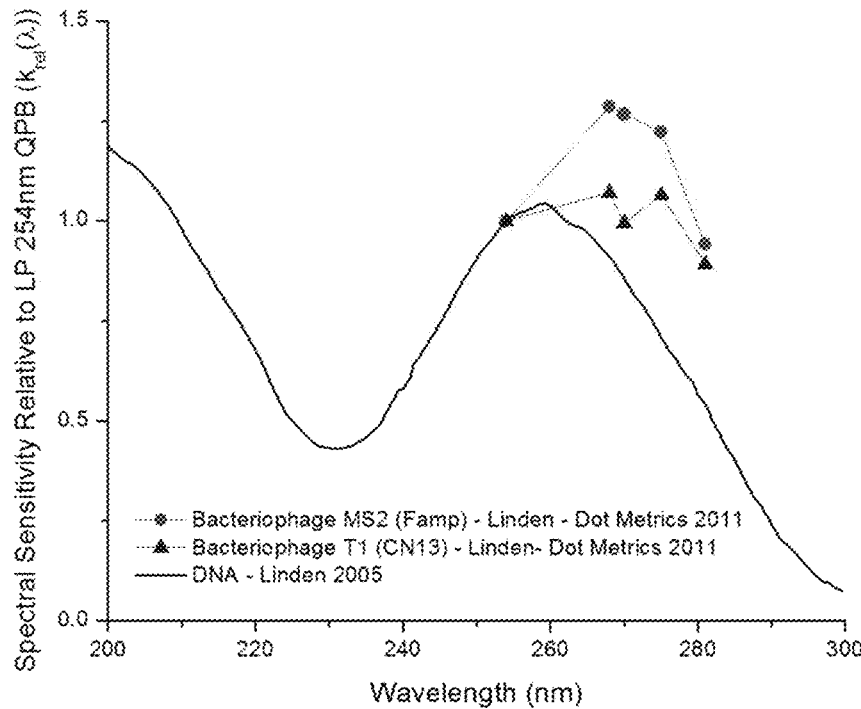
FIG. 4 is a plot illustrating enhanced UV inactivation in coliphage MS2 at about 270 nm.

Research conducted using an experimental LV LED collimated beam apparatus with selectable wavelengths varying from about 255 to about 285 nm indicated an enhanced UV inactivation in coliphage MS2 when targeting adenine-thymine pairs with about 270-nm photons with respect to the UV inactivation obtained with about 254-nm photons from a low pressure Hg lamp, as illustrated in FIG. 4.

Commercially available, individual UV-C LED chips (UV LEDs with a peak emission <about 300 nm) typically provide less than about 3 mW of optical power, however, multi-chip packages can be assembled to increase the optical output power to values as high as about 120 mW. UV-C LEDs can be packaged in a variety of configurations, including watertight hermetic packages having a diameter ranging about 5 mm to about 5 cm. A typical UV-C LED operates with a rapid (<about 1 s with ordinary electronic drivers) power-on time at around 6 V and around 20 mA. These efficiencies make UV-C LEDs ideal candidates for battery or solar powered applications.

UV-C LEDs first emerged as research grade devices in the late 1990's, and currently suffer from technological immaturity. The highest external quantum efficiency (EQE) reported in the literature to date is about 11%, however, commercial grade UV-C LEDs feature an EQE of less than about 4%, indicating that over about 96% of the input electrical energy is wasted as heat. Driven by the need to improve overall efficiency and performance, UV-C LED manufacturers mainly focus on the challenging obstacles raised by device structures and materials. Little or no effort has been made to innovate the packaging of UV-C LEDs, which have unique needs and requirements that differ from those of visible light emitting LEDs. UV-C LEDs require materials that will not absorb UV-C radiation, and packages that can manage excess heat. Thus, commercially available devices maintain obsolete packaging options, which are meant to be used for visible LEDs.

The current state of the world's energy and water constraints, along with chemical and biological contamination concerns, create a business environment poised for an affordable, compact, and energy efficient fluid disinfection system. Similarly, concerns over antibiotic resistant respiratory infections arising from airborne pathogens are worsening. The present invention provides a reduction in device operating temperature, resulting in significantly higher light generation efficiency and longer operating life, combined with a significant improvement in photon extraction efficiency translating into a greater than 30% gain in optical output power in a reduced footprint as compared to currently available legacy packages. The footprint reduction enables a broader field of applications and, more importantly, the reduction of the devices per UV-C LED lamp drives down the system costs by > about 30% for disinfection flow cells.

The reduced footprint and the rapid on-off operation of UV LEDs allow their integration into compact UV induced fluorescence detection systems for aerosolized biological particles. Biological materials ubiquitously contain the coenzyme nicotinamide adenine dinucleotide (NADH), which exhibits optical absorption within the range of about 330-350 nm, and amino acid tryptophan, which readily absorbs radiation within a range of about 270-290 nm. These compounds exhibit characteristic fluorescence emission spectra, which enables discrimination between biological and non-biological particles. The proposed innovation is that UV LEDs having multiple wavelengths, including about 270-290 nm and about 330-350 nm, can be integrated into a source and detector module. Said module detects the presence of biological particles in a fluid, and communicates this information to a configurable UV radiation source, such as a selectively controllable matrix of UV LED dice with a varying peak emission wavelengths, which provides optimized disinfection. By this method, a biological pathogen such as anthrax could be identified and more efficiently neutralized by dynamic configuration of the UV source.

Figure 5:
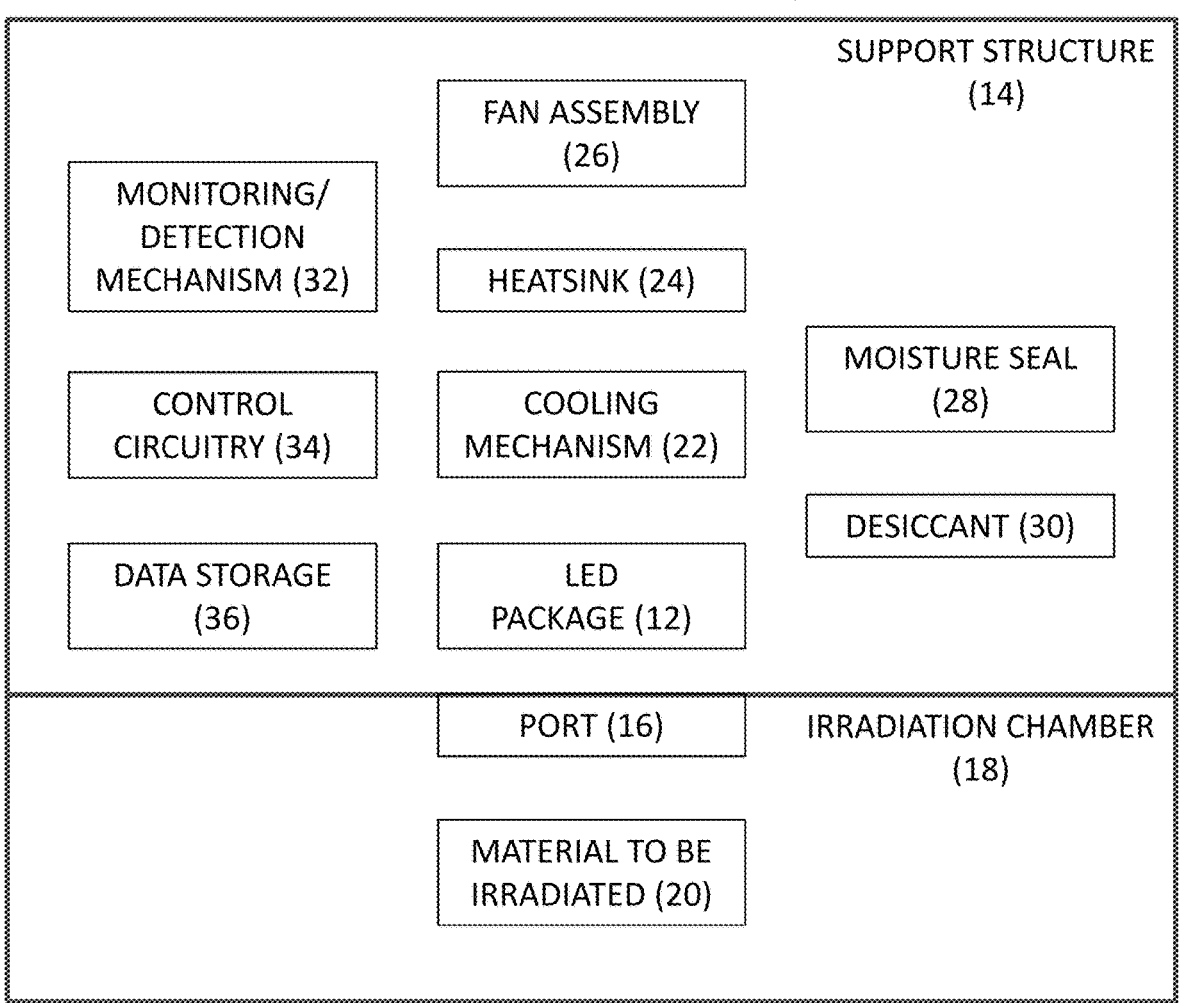
FIG. 5 is a schematic diagram illustrating one exemplary embodiment of the irradiation apparatus of the present invention.
Figure 6:
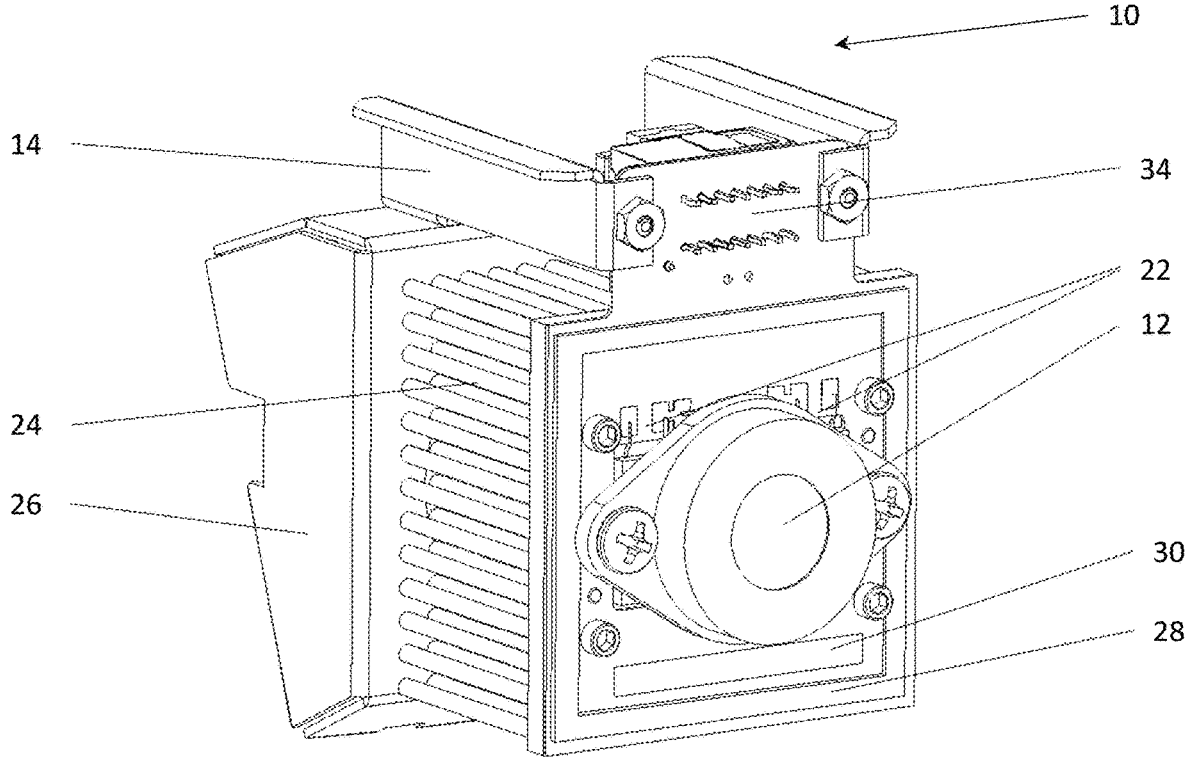
FIG. 6 is a perspective view illustrating one exemplary embodiment of the irradiation apparatus of the present invention.
Figure 7:
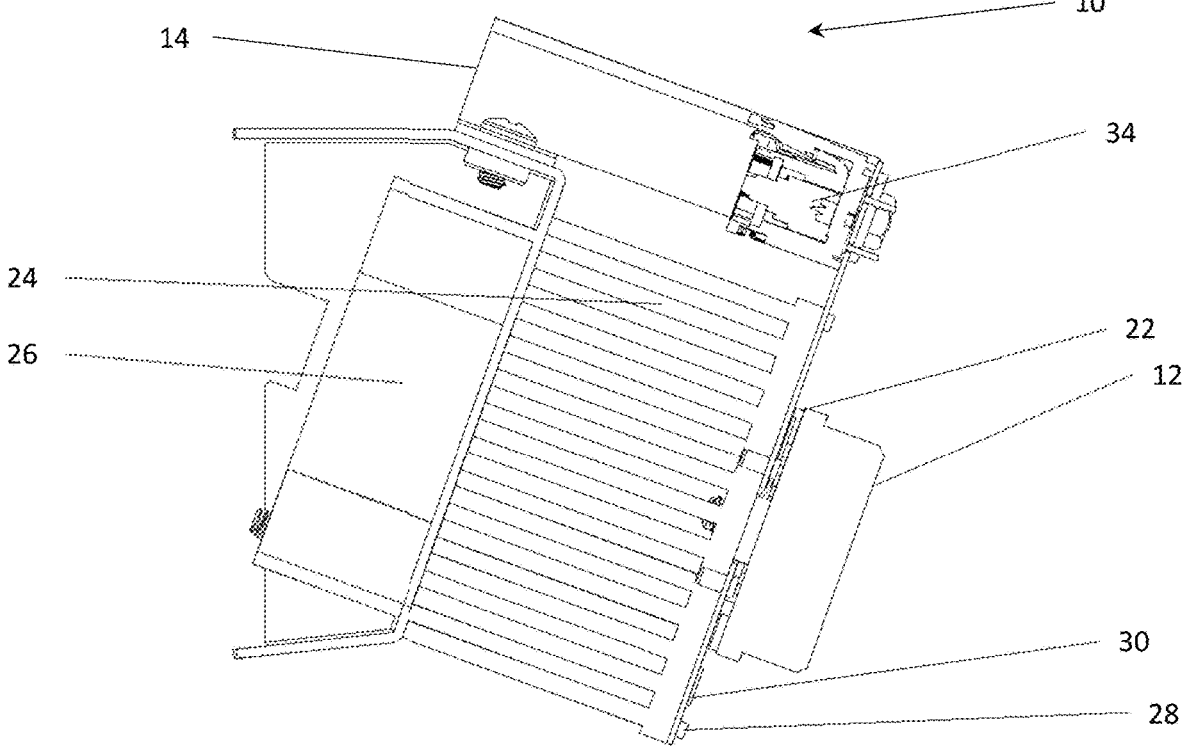
FIG. 7 is a planar side view illustrating one exemplary embodiment of the irradiation apparatus of the present invention.
Figure 8:
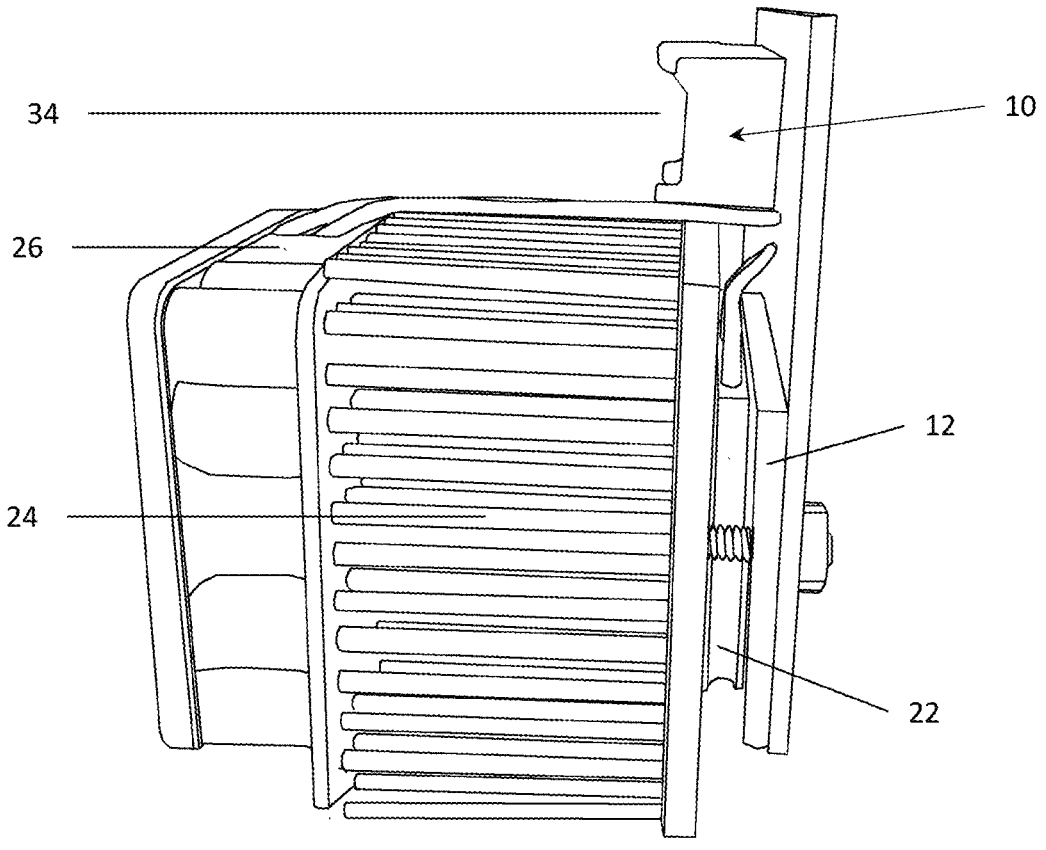
FIG. 8 is a perspective view illustrating another exemplary embodiment of the irradiation apparatus of the present invention.
Figure 9:
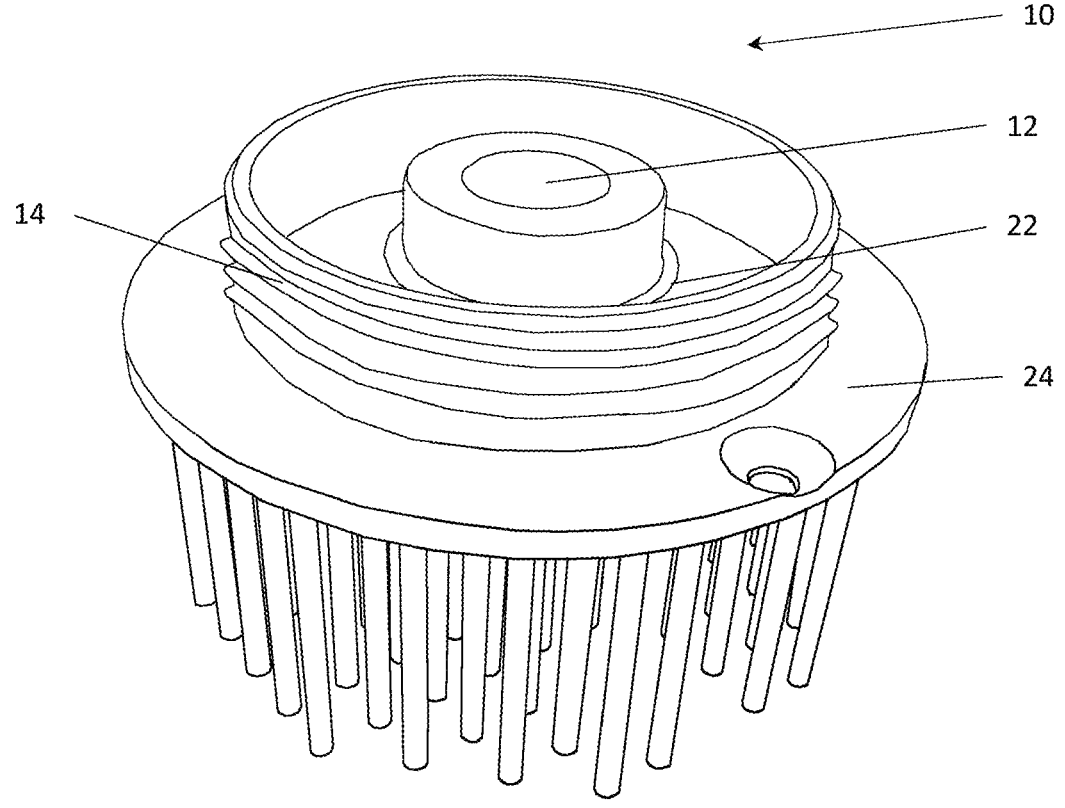
FIG. 9 is a perspective view illustrating a further exemplary embodiment of the irradiation apparatus of the present invention.

The present invention also enables bandgap electric photo-excitation in n-type single crystalline semiconductors, such as titanium oxide ($TiO2$), zinc oxide ($ZnO$), and tin oxide ($SnO2$). When such semiconductors are in contact with an electrolyte in water, electrons are transferred from the semiconductor to the electrolyte until the potentials reach equilibrium. Under irradiation with photons with energy equivalent to or larger than that of the semiconductor's bandgap, electron-hole pairs are generated in the semiconductor, hence altering the equilibrium of the potentials. The electron-hole pairs diffuse to the surface of the semiconductor where they may quickly recombine, or may be captured by molecules of water species present on the surface of the semiconductor, resulting in the photocatalytic splitting of water and the generation of OH radicals, which participate in the destruction of organic compounds. Water disinfection can be achieved using this method. The radiation emission of LED dice can be tailored so that the energy of the emitted photons matches that of a given n-type crystalline semiconductor to optimize the photocatalytic effect. Multiple wavelengths can also be used simultaneously to enable the bandgap electronic photo-excitation in n-type single crystalline semiconductors, DNA nucleotide dimerization, and saturate the absorption mechanism of nucleocapsids. For example, different wavelengths can be used to simultaneously saturate the absorption mechanism of nucleocapsids (absorption peak centered at around 280 nm), target the peak absorption of nucleic acid (peak absorption centered at around 265 nm), and enable electron transfer from semiconductor to electrolyte with photons having energy equivalent to or larger than that of the semiconductor's bandgap Thus, referring now specifically to FIG. 5, in one exemplary embodiment of the present invention, the gas/liquid/solid irradiation apparatus 10 includes a LV radiation source 12 (or a plurality of UV radiation sources 12) coupled to a support structure 14. The support structure 14 holds the UV radiation source(s) 12, which may be UV-C radiation source(s) 12, such that they selectively direct UV radiation through a port 16 and into the interior of an irradiation chamber 18 in which a material to be irradiated 20 is selectively disposed. As described herein above and below, peak wavelengths may be (dynamically) selected and a plurality of wavelengths may be utilized such that the action spectrum of a given organism can be targeted, thus improving disinfection efficiency. Optionally, as described herein above, the material to be irradiated 20 may be disposed adjacent to an n-type single crystalline semiconductor to generate hydrogen peroxide at the semiconductor surface through bandgap electric photo-excitation for disinfection. Heat is managed, and optionally recuperated, using a cooling mechanism 22, heatsink 24, and fan assembly 26 disposed substantially adjacent to the UV radiation source(s) 12, and the irradiation apparatus 10 may be made moisture resistant using a moisture seal 28 and desiccant 30 coupled to and/or disposed within the support structure 14. The irradiation assembly can include a monitoring/detection mechanism 32 and control circuitry 34 for dynamically controlling the delivery of UV radiation to the material to be irradiated 20 based upon its identification. Finally, associated performance data may be stored in an onboard or external data storage unit 36.

Figure 10:
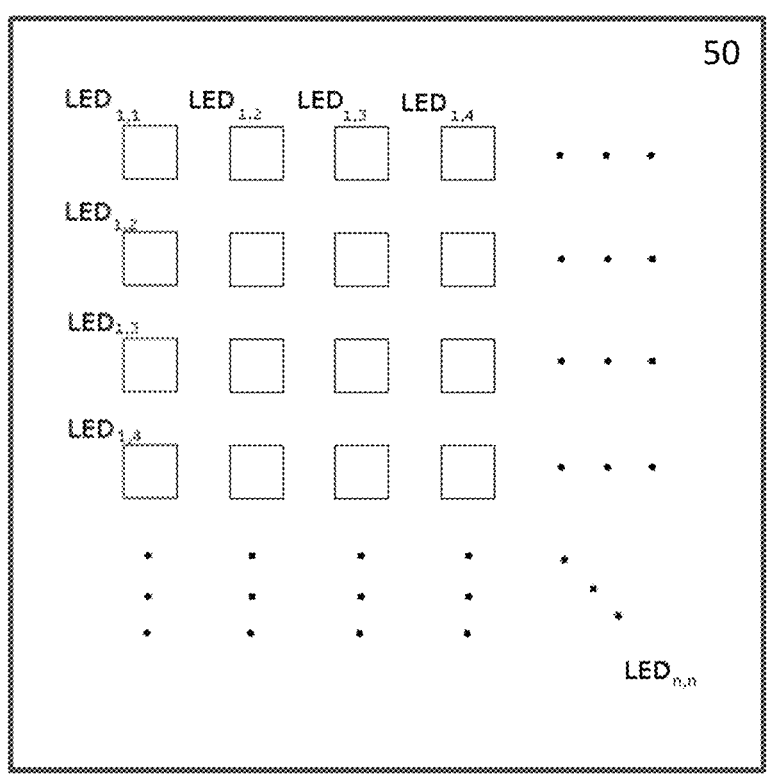
FIG. 10 is a schematic diagram illustrating one exemplary embodiment of an array of UV radiation sources that may be used in conjunction with the irradiation apparatus of the present invention.

Referring now specifically to FIGS. 6-10, in various exemplary embodiments of the present invention, a modular semiconductor UV LED mounting configuration 10 is provided including a UV radiation source package 12 containing a single LED or multiple LED "dice" arranged in a matrix or array 50, as illustrated in FIG. 10. The LED dice can be selected to provide multiple wavelengths in both the UV and visible radiation spectrum from about 200 nm to about 800 nm. In one exemplary embodiment, the matrix or array 50 includes LED dice emitting wavelengths in the range of about 200-320 nm in order to saturate the absorption mechanism of nucleocapsids (with peak emission centered at around 280 nm), and at the same time to target the peak absorption of nucleic acid with its peak emission wavelength spanning about 250-280 nm. In another exemplary embodiment, with the intention of mimicking the optical output spectrum of low or medium pressure Hg-based UV lamps used to target various bacteria and viruses, the matrix or array 50 of LED dice utilizes multiple wavelengths, including at least one of about 240-260 nm, about 260 nm-344 nm, about 350-380 nm, about 400-450 nm, or about 500-600 nm. A further exemplary embodiment is a matrix or array 50 of LED dice emitting germicidal wavelengths ranging from about 250 nm to 300 nm in conjunction with LED dice emitting wavelengths in the range of about 350 nm to 400 nm to enable photocatalytic oxidation of pathogens or pollutants in water in proximity of crystalline films of n-type semiconductors, such as $TiO_2$, NiO, or $SnO_2$. A still further exemplary embodiment is a modular mounting configuration containing multiple LED dice emitting about 250-320 nm and about 320-400 nm wavelengths arranged in a matrix or array to enable the fluorescence spectra of NADH, and tryptophan, of particles with biological origin. In another exemplary embodiment, a commercially available SETi UTV Clean™ LED package is used. Individual LED dice or a single die bonded to a thermally conductive metal core circuit board (MCPCB), such as those available from The Bergquist Company™, may also be used.

The LED package 12 is connected to a heat dissipation sink 24, which is in turn configured to mount to a window port 16 of an irradiation chamber 18. The mounting face of the module 10 possesses a seal or gasket 28, which encloses the LED package 12 along with a desiccant 30, thus reducing condensing moisture. The heatsink 24 may be round, square, or another suitable shape. Heat from the LEDs is optionally conducted by the aid of a thermoelectric cooler 22 or other means to the heatsink 24, which is optionally cooled by forced air 26. The LED package 12 is electrically connected to control and power circuitry 34, which is included as part of the replaceable module 10. Circuitry 36 is included within the replaceable module 10 in order to provide telemetric data and track information, such as operating temperature and run time.

Thus, a packaged UV LED 12, or a matrix or array of multiple UV LEDs 50, are attached to a heatsink 24. Multiple UV wavelengths can be used to optimize the effect on specific microorganisms. Backside heat extraction is aided by thermoelectric cooling (TEC) 22 and/or a vapor chamber, Additionally, the UV LED package 12 is topside cooled by conduction through a highly thermally conductive over-layer, such as silicone polymer impregnated with diamond nanoparticles, which may have a single crystalline structure.

The surface of the metal portion of the heatsink 24 and UV radiation emitting housing 14 may be flat for mounting the LED and accessory dies or packages 12, 50; or optionally recessed in order to provide a concave reflective structure for the LEDs and/or to provide means for attachment. The heatsink 24 may be attached to the irradiation apparatus 10 by a variety of methods, including, but not limited to, spring pins, clamps, clips that swivel, screws, by screwing in an exemplary embodiment of the heatsink 24 with a rounded bezel that has threads cut into it (FIG. 9), or by twisting in an exemplary embodiment of the heatsink 24 with a rounded bezel which connects by means of a bayonet connector.

The radiation emitter module 10 is a user replaceable unit, optionally including attached electronics and desiccating materials in order to combat moisture and humidity. Attached electronics can include an individual identification number and telemetry tracking, as well as an interconnect for easy disconnect from a larger system.

Cooling of the LED package 12 may be assisted by a TEC or vapor chamber 22 that is situated between the LED package 12 and the heatsink 24. The TEC may take the form of a single TEC, or multiple modules situated to provide contact around irregular package geometry, such as a through-hole design. Furthermore, electro-thermal modules may be included to harvest energy from the waste heat created.

The UV radiation is transmitted from the LED dice through a transmissive window, polymer, air, and/or aperture 16 into the irradiation chamber 18. The transmissive window 16 has a transmission spectrum appropriate for the choice of LEDs used, for example the UV-C range.

Although the present invention is illustrated and described herein with reference to preferred embodiments and specific examples thereof, it will be readily apparent to those of ordinary skill in the art that other embodiments and examples may perform similar functions and/or achieve like results. Likewise, it will be apparent that various applications of the disclosed technology are possible. All such equivalent embodiments, examples, and applications are within the spirit and scope of the present invention, are contemplated thereby, and are intended to be covered by the following claims.

What is claimed is:

1. A liquid irradiation system comprising:
   a flow cell irradiation chamber having an interior space for containing a liquid to be irradiated, the flow cell irradiation chamber including an irradiation passage comprising at least one of a window port and an aperture; and
   an irradiation apparatus comprising:
      a support structure coupled to the flow cell irradiation chamber;
      an ultraviolet (UV) light radiation source package coupled to the support structure, the UV light radiation source package comprising one or more UV-C LED radiation sources bonded to a thermally conductive metal core circuit board (MCPCB), the UV light radiation source package mounted to the irradiation passage and optically coupled to the flow cell irradiation chamber through the irradiation passage in the flow cell irradiation chamber, for directing UV radiation into the interior space of the flow cell irradiation chamber and into the liquid to be irradiated; and a heat exchange cooling mechanism thermally coupled to the one or more UV-C LED radiation sources, wherein the heat exchange cooling mechanism is disposed adjacent to the one or more UV-C LED radiation sources opposite the interior space of the flow cell irradiation chamber, and the heat exchange cooling mechanism removes heat by conduction or convection from the one or more UV-C LED radiation sources and transfers the heat to an environment external to the liquid irradiation system.

2. The liquid irradiation system of claim 1, wherein the heat exchange cooling mechanism comprises one or more of a thermoelectric cooling device, a vapor chamber, a heatsink, a heat dissipation structure, a fan, a material thermally coupled to a fluid, and a cooling coating.

3. The liquid irradiation system of claim 1, wherein the heat exchange cooling mechanism further comprises a heat recovery mechanism.

4. The liquid irradiation system of claim 1, further comprising a moisture seal and desiccant disposed adjacent to the one or more UV-C LED radiation sources.

5. The liquid irradiation system of claim 1, wherein the one or more UV-C LED radiation sources comprise a plurality of UV-C LED radiation sources arranged in an array.

6. The liquid irradiation system of claim 1, wherein one or more wavelengths of the one or more UV-C LED radiation sources are dynamically adjustable.

7. The liquid irradiation system of claim 1, wherein one or more wavelengths of the one or more UV-C LED radiation sources are selected based on an identification of a contaminant in the liquid to be irradiated.

8. The liquid irradiation system of claim 7, wherein the one or more UV-C LED radiation sources deliver one or more wavelengths to the liquid to be irradiated that induce fluorescence in the liquid to be irradiated.

9. The liquid irradiation system of claim 1, wherein the one or more UV-C LED radiation sources deliver a combination of wavelengths to the liquid to be irradiated.

10. The liquid irradiation system of claim 1, wherein one or more wavelengths of the one or more UV-C LED radiation sources are selected to both saturate an absorption mechanism in the liquid to be irradiated and target a peak absorption in the liquid to be irradiated.

11. The liquid irradiation system of claim 1, wherein the one or more UV-C LED radiation sources deliver one or more wavelengths to a semiconductor material disposed substantially adjacent to the liquid to be irradiated thereby causing a disinfection agent to be generated in proximity of the liquid to be irradiated.

12. The liquid irradiation system of claim 1, further including a radiation intensity feedback mechanism for dynamically controlling delivery of UV-C LED radiation to the liquid to be irradiated.

13. The liquid irradiation system of claim 1, further including a source and detector module that detects presence of biological particles and communicates with the one or more UV-C LED radiation sources.

14. The liquid irradiation system of claim 1, further comprising a radiation intensity feedback mechanism, wherein the radiation intensity feedback mechanism comprises at least one of a photodiode or a CCD.

15. A liquid irradiation system comprising:

a flow cell irradiation chamber having an interior space for containing a liquid to be irradiated, the flow cell irradiation chamber including an irradiation passage comprising a window port and an aperture; and an irradiation apparatus comprising:

a support structure coupled to the flow cell irradiation chamber;

an ultraviolet (UV) light radiation source package coupled to the support structure, the UV light radiation source package comprising a plurality of UV LED radiation sources bonded to a thermally conductive metal core circuit board (MCPCB), the UV light radiation source package mounted to the irradiation passage and optically coupled to the flow cell irradiation chamber through the irradiation passage in the flow cell irradiation chamber, so UV radiation from the plurality of UV LED radiation sources is directed into the interior space of the flow cell irradiation chamber through the window port and the aperture of the irradiation passage; and a heat exchange cooling mechanism thermally coupled to the plurality of UV LED radiation sources, wherein the heat exchange cooling mechanism is disposed adjacent to the plurality of UV LED radiation sources opposite the interior space of the flow cell irradiation chamber, and the heat exchange cooling mechanism removes heat by conduction or convection from the plurality of UV LED radiation sources and transfers the heat to an environment external to the liquid irradiation system.

16. The liquid irradiation system of claim 15, wherein the plurality of UV LED radiation sources comprises a plurality of UV-C LEDs.

17. The liquid irradiation system of claim 15, wherein the heat exchange cooling mechanism comprises a heatsink.

18. The liquid irradiation system of claim 15, wherein further comprising a radiation intensity feedback mechanism.

19. The liquid irradiation system of claim 18, wherein the radiation intensity feedback mechanism comprises at least one of a photodiode or a CCD.

* * * * *